(12) United States Patent
Nagai

(10) Patent No.: US 10,393,651 B2
(45) Date of Patent: Aug. 27, 2019

(54) ATTACHMENT FOR LIQUID SAMPLE MEASUREMENT, REFRACTIVE INDEX MEASURING DEVICE AND REFRACTIVE INDEX MEASURING METHOD

(71) Applicant: SHIMADZU CORPORATION, Kyoto (JP)

(72) Inventor: Tetsuya Nagai, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 16/100,225

(22) Filed: Aug. 10, 2018

(65) Prior Publication Data

US 2019/0094138 A1    Mar. 28, 2019

(30) Foreign Application Priority Data

Sep. 26, 2017 (JP) ................................. 2017-185297

(51) Int. Cl.
*G01N 21/03* (2006.01)
*G01N 21/41* (2006.01)

(52) U.S. Cl.
CPC ......... *G01N 21/4133* (2013.01); *G01N 21/03* (2013.01); *G01N 2021/4146* (2013.01); *G01N 2021/4153* (2013.01)

(58) Field of Classification Search
CPC ............................ G01N 21/4133; G01N 21/03

USPC .................................................. 356/134, 246
See application file for complete search history.

(56) References Cited

U.S. PATENT DOCUMENTS

| | | | | |
|---|---|---|---|---|
| 3,779,648 A | * | 12/1973 | Poster | .................... G02C 13/00 356/124 |
| 4,332,471 A | * | 6/1982 | Gross | ..................... G01N 21/03 356/246 |
| 2014/0306640 A1 | | 10/2014 | Yamamoto | |
| 2015/0338343 A1 | * | 11/2015 | Huang | .................. G01M 3/047 356/70 |
| 2018/0067288 A1 | * | 3/2018 | Huang | ............... G01N 21/4133 |

FOREIGN PATENT DOCUMENTS

JP        2014207809        10/2014

* cited by examiner

*Primary Examiner* — Roy M Punnoose
(74) *Attorney, Agent, or Firm* — JCIPRNET

(57) ABSTRACT

Provided are an attachment for liquid sample measurement which is capable of effectively reducing a consumption amount of a liquid sample, a refractive index measuring device and a refractive index measuring method. An attachment (100) is disposed on a V-block prism (1) formed on a V-shaped groove (11) for keeping a sample so as to enter the groove (11). A body (110) of the attachment (100) forms an enclosing space (107) for enclosing the liquid sample between the body and a surface of the groove (11) formed on the V-block prism (1), and makes the liquid sample enclosed in the enclosing space (107) contact directly with the surface of the groove (11).

7 Claims, 9 Drawing Sheets

ATTACHMENT FOR LIQUID SAMPLE MEASUREMENT, REFRACTIVE INDEX MEASURING DEVICE AND REFRACTIVE INDEX MEASURING METHOD

CROSS-REFERENCE TO RELATED APPLICATION

This application claims the priority benefit of Japan Application no. 2017-185297, filed on Sep. 26, 2017. The entirety of the above-mentioned patent application is hereby incorporated by reference herein and made a part of this specification.

BACKGROUND

Technical Field

The disclosure relates to an attachment for liquid sample measurement which is disposed on a V-block prism with a V-shaped groove for keeping a sample formed thereon so as to enter the groove, and which is used when a refractive index of a liquid sample is measured by a V-block refractive index measuring device, a refractive index measuring device and a refractive index measuring method.

Description of Related Art

In the V-block refractive index measuring device which is an example of the refractive index measuring device, a sample is mounted on a V-shaped groove formed on a V-block prism, and a measuring beam is irradiated to the sample via the V-block prism. Then, the measuring beam emitted from the V-block prism with an angle corresponding to a wavelength is scanned at a specific range and detected by a detector, thereby measuring the refractive index of the sample based on the detection result (for example, see patent literature 1 below).

In a case that this kind of refractive index measuring device is used to measure the refractive index of a liquid sample, for example, a V-block prism for liquid sample is used. In the V-block prism for liquid sample, a V-shaped groove is formed as in a V-block prism for solid sample, and a side surface wall which blocks a side of the groove is arranged so that the liquid sample does not leak from the groove. By injecting the liquid sample into the groove of which the side is blocked by the side surface wall, the liquid sample can be kept at the V-block prism.

Besides, as another method for measuring the refractive index of the liquid sample, the following method is known in which the liquid sample is filled in a cell and the cell is mounted the groove of a V-block prism for solid sample. In this method, the cell is mounted on the V-block prism so that the liquid sample is filled in a rectangular or cubic hollow cell, and a corner an external wall surface of the cell follows the V-shaped groove of the V-block prism.

LITERATURE OF RELATED ART

Patent Literature

[Patent literature 1] International Publication No. 2014/207809

Problems to be Solved

In a case that a V-block prism for liquid sample is used, liquid sample is injected into a V-shaped groove which has a relatively large volume, so that consumption amount of the liquid sample is large. Although the method in which liquid sample is filled in the cell can decrease the volume of the cell, there is a limit in the decreasing of the volume, so that the consumption amount of the liquid sample cannot be effectively reduced.

SUMMARY

The disclosure provides an attachment for liquid sample measurement which can effectively reduce the consumption amount of the liquid sample, a refractive index measuring device and a refractive index measuring method.

Means to Solve the Problems

An attachment for liquid sample measurement of the disclosure is disposed on a V-block prism with a groove which is a V-shaped groove for keeping a liquid sample formed thereon so as to enter the groove, and is used when a refractive index of a liquid sample is measured by a V-block refractive index measuring device, the attachment for liquid sample measurement including a body. The body forms an enclosing space for enclosing the liquid sample between the body and a surface of the groove formed on the V-block prism, and makes the liquid sample enclosed in the enclosing space contact directly with the surface of the groove.

A refractive index measuring device of the disclosure includes the attachment for liquid sample measurement, a V-block prism, a light source part and a detector. The attachment for liquid sample measurement is disposed on the V-block prism. The light source part irradiates a measuring beam to the liquid sample enclosed in the enclosing space via the V-block prism. The detector detects the measuring beam transmitted through the liquid sample.

A refractive index measuring method of the disclosure includes an attachment disposing step and a measuring step. In the attachment disposing step, the attachment for liquid sample measurement is disposed on the V-block prism, on which the V-shaped groove for keeping the liquid sample is formed, so as to enter the groove, thereby forming an enclosing space which encloses the liquid sample between the surface of the groove formed on the V-block prism and the attachment for liquid sample measurement. In the measuring step, the measuring beam is irradiated, via the V-block prism, to the liquid sample which is enclosed in the enclosing space so as to contact directly with the surface of the groove, thereby detecting the measuring beam transmitted through the liquid sample and measuring the refractive index of the liquid sample.

DESCRIPTION OF THE EMBODIMENTS

An Overall Structure of a Refractive Index Measuring Device

Figure 1:
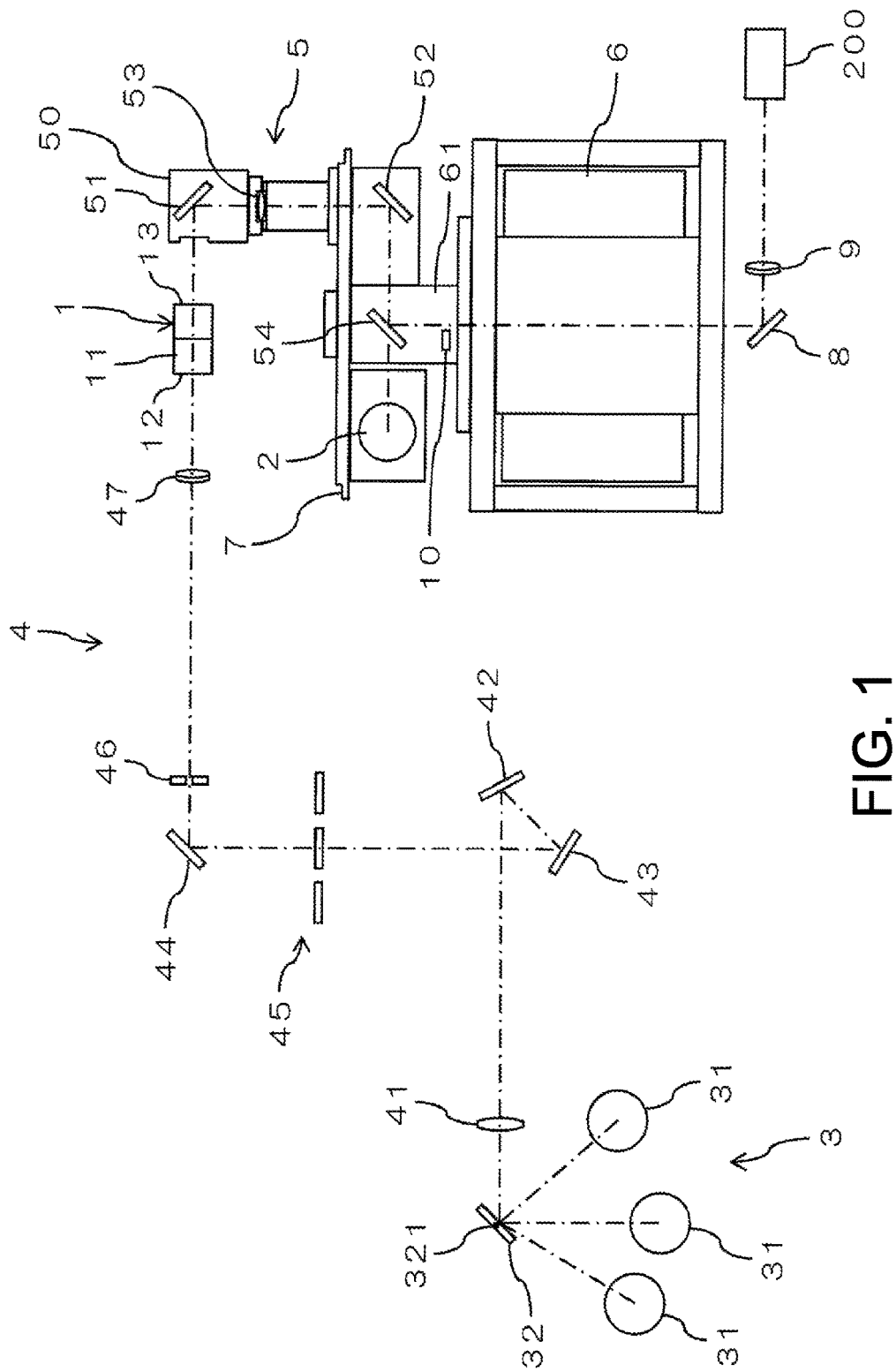
FIG. 1 is a schematic plan view illustrating a configuration example of a refractive index measuring device according to an embodiment of the disclosure.

FIG. 1 is a schematic plan view illustrating a configuration example of a refractive index measuring device according to an embodiment of the disclosure. The refractive index measuring device is a V-block refractive index measuring device which measures a refractive index of a sample by irradiating a measuring beam to the sample via a V-block prism 1.

The sample may be, for example, glass, plastic or liquid and so on, and in the embodiment, a case that the refractive index of a liquid sample is measured is described. The liquid sample is kept in a V-shaped the groove 11 (FIG. 1 is a diagram illustrating the groove 11 from right above) formed on the V-block prism 1, the measuring beam transmitted through the liquid sample is detected by a detector 2, and the refractive index of the liquid sample can be measured according to a calculated refraction angle and the refractive index of the V-block prism 1.

The refractive index measuring device is provided with, in addition to the V-block prism 1 and the detector 2, a light source part 3 which irradiates the measuring beam, a first optical system 4 which guides the measuring beam from the light source part 3 to the V-block prism 1, and a second optical system 5 which guides the measuring beam transmitted through the V-block prism 1 to the detector 2.

The light source part 3 is provided with a plurality of light sources 31. Helium lamp, hydrogen lamp and mercury lamp for example may be used as the light source 31, and the measuring beam with different wavelengths such as a helium d-ray, a hydrogen C-ray, a hydrogen F-ray, a mercury e-ray, a mercury g-ray and a mercury h-ray can be irradiated from the light source part 3. The measuring beam from the light source 31 is reflected by a mirror 32 and irradiated from the light source part 3 in a horizontal direction. The mirror 32 can rotate around a rotation axis 321 extending along a vertical direction (forward-backward direction in FIG. 1), and can guide the measuring beam originated from the light source 31 corresponding to a rotation position of the mirror 32 to the first optical system 4. However, the light source 31 is not limited to the types as mentioned above.

The first optical system 4 is provided with a lens 41, mirrors 42, 43, 44, a filter 45, a slit 46, a collimator lens 47 and so on. The measuring beam from the light source part 3 passes through the lens 41, reflects at the mirrors 42 and 43 in sequence and then incident into the filter 45.

A plurality of filters 45 are arranged, and by inserting a filter 45 chosen in accordance with the type of the light source 31 into the light path, only the measuring beam of a specific wavelength corresponding to the filter 45 (monochromatic light) transmits through the filter 45 and is guided to the mirror 44 side. The measuring beam reflected at the minor 44 passes the slit 46 and is converted by the collimator lens 47 into parallel light, then is incident on the V-block prism 1. The measuring beam incident on the V-block prism 1 from an end surface 12 transmits through the liquid sample kept in the V-shaped groove 11, then passes through the V-block prism 1 again and is emitted from the other end surface 13.

The second optical system 5 is provided with mirrors 51, 52, a telemeter lens 53, a beam splitter 54 and so on. The second optical system 5 is fixed to a disk 7 attached to a rotation axis 61 of a motor 6. Specifically, the mirrors 51, 52 and the telemeter lens 53 are fixed to the disk 7 so as to be arranged in parallel to the rotation axis 61 at a position eccentric to the rotation axis 61, and the mirror 52 and the beam splitter 54 are fixed to the disk 7 so as to be arranged in a vertical direction with respect to the rotation axis 61.

The mirror 51 is disposed so that a reflection surface slopes 45° with respect to an incident direction of the measuring beam, by which the measuring beam reflected at the mirror 51 changes a progressing direction for 90° and is guided to the telemeter lens 53. The telemeter lens 53 focuses the measuring beam from the V-block prism 1 and guides the measuring beam to the mirror 52, and the measuring beam reflected at the mirror 52 transmits through the beam splitter 54 and is received by the detector 2 fixed to the disk 7. The detector 2 detects an intensity of the measuring beam transmitted through the sample by outputting a signal corresponding to an intensity of the received beam.

The mirror 51 and the telemeter lens 53 are disposed in a row in the vertical direction with respect to the incident direction of the measuring beam from the V-block prism 1, and are integrally kept on the disk 7 as a telemeter part 50 at a position eccentric to the rotation axis 61. Therefore, if the disk 7 is rotated around the rotation axis 61 by rotating the motor 6, the position of the telemeter part 50 with respect to the V-block prism 1 is changed (scanned), the measuring beam from the V-block prism 1 can be received from different angles and be guided to the detector 2. The motor 6 includes a sub-motor with an encoder for example and can accurately get the rotation angle of the motor 6.

On the other hand, the measuring beam reflected at the beam splitter 54 passes through the lens 9 after being reflected at the mirror 8 and is guided to a camera 200, and the measuring beam transmitted through the sample can be imaged by the camera 200. The beam splitter 54 and the mirror 8 are arranged on the rotation axis 61, and when the position of the V-block prism 1 is adjusted, an auto-collimation prism 10 can be inserted in the light path between the beam splitter 54 and the mirror 8.

The camera 200 can be formed by, for example, a Charge Coupled Device (CCD) camera. The camera 200 is not limited to the structure arranged on the position as mentioned above, and may be, for example, such a structure that the measuring beam is guided to the camera 200 via a beam splitter which is attached to the disk 7 and is arranged separated from the beam splitter 54, or may be a structure in which more than two cameras 200 are arranged.

2. Structure of the V-block Prism and the Attachment

Figure 2:
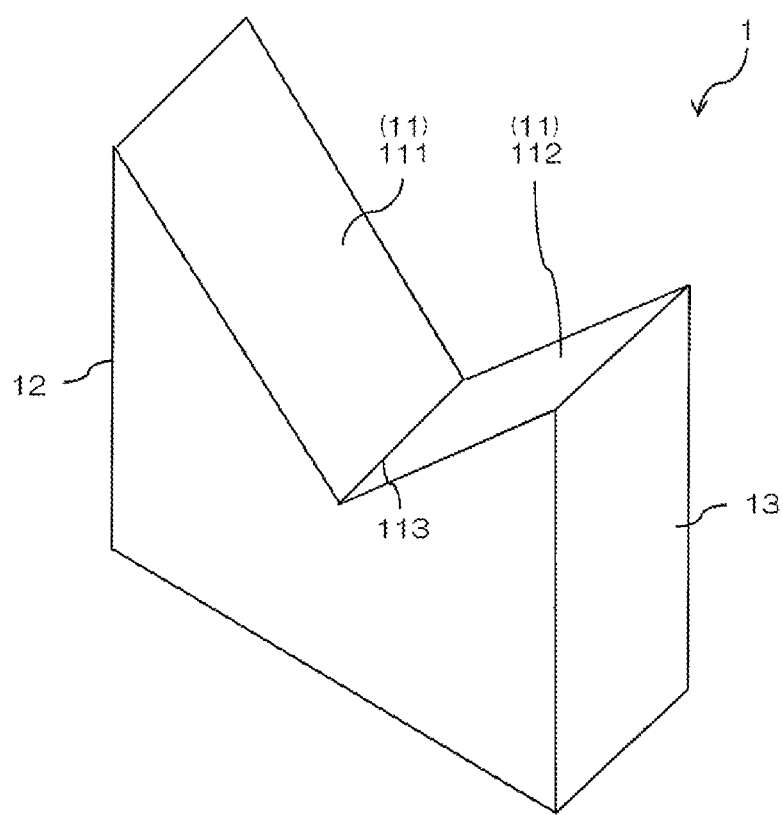
FIG. 2 is a perspective view illustrating a configuration example of a V-block prism.

FIG. 2 is a perspective view illustrating a configuration example of the V-block prism 1. As shown in FIG. 2, the V-block prism 1 is provided with the V-shaped the groove 11 formed by a pair of plane surfaces 111, 112 at right angles to each other. In the embodiment, by disposing the attachment for liquid sample measurement on the groove 11 of the V-block prism 1, the liquid sample can be kept in the groove 11.

Figure 3A:
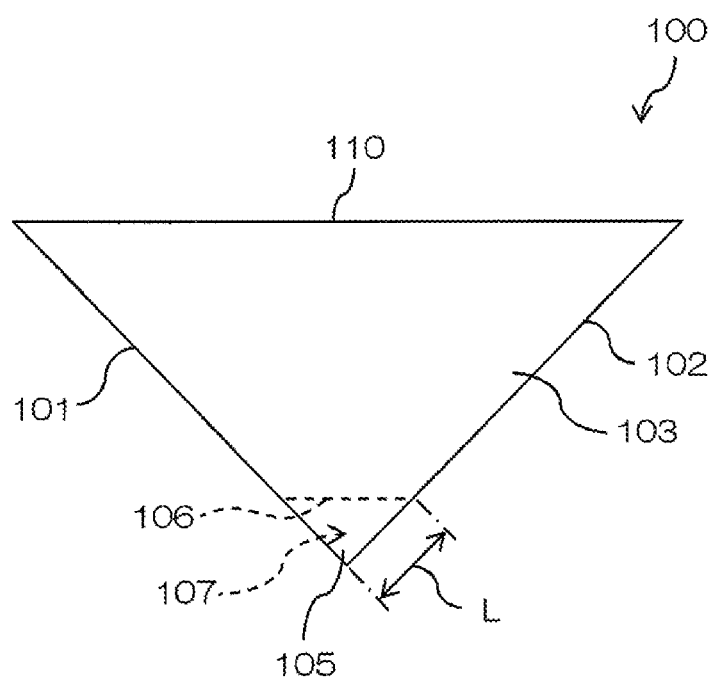
FIG. 3A is a front view illustrating an example of an attachment.
Figure 3B:
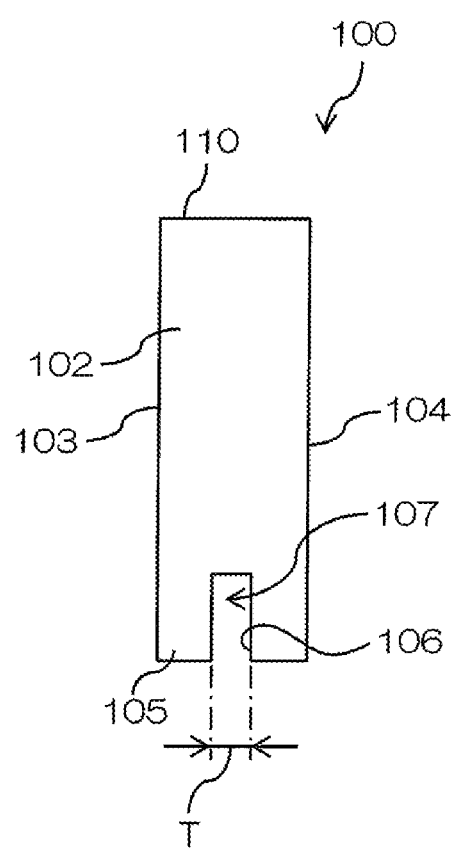
FIG. 3B is a side view of the attachment in FIG. 3A.
Figure 4:
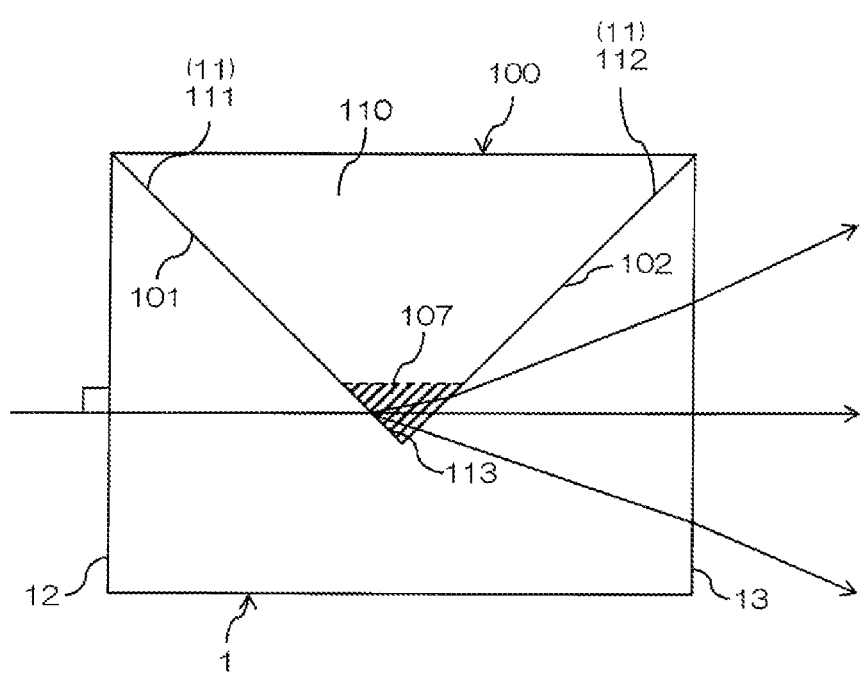
FIG. 4 is a front view illustrating a state that the attachment in FIG. 3A is disposed on a groove of a V-block prism.

FIG. 3A is a front view illustrating an example of an attachment 100. FIG. 3B is a side view of the attachment 100 in FIG. 3A. FIG. 4 is a front view illustrating a state that the attachment 100 in FIG. 3A is disposed on the groove 11 of the V-block prism 1. The attachment 100 is used when the refractive index of the liquid sample is measured with a refractive index measuring device, and as shown in FIG. 4, is disposed so as to enter the groove 11 of the V-block prism 1 (attachment disposing step).

A body 110 of the attachment 100 has a shape of a triangular prism. Specifically, the body 110 includes a pair of side surfaces 101, 102 at right angle to each other, and a front surface 103 and a rear surface 104 which are both triangle-shaped. The pair of side surfaces 101, 102 of the body 110 are formed to a V-shape corresponding to the groove 11, and the body 110 is mounted on the groove 11 in a state that the side surface 101 contacts with a plane surface 111 of the groove 11 and the side surface 102 contacts with a plane surface 112 of the groove 11.

A part in the body 110 where the side surfaces 101 meets with the side surfaces 102 forms a V-shaped pointed top 105. In the top 105 of the body 110, a recess 106 which sinks in parallel with the front surface 103 and the rear surface 104 toward a central part side of the body 110 is formed. On the other hand, a part in the groove 11 where the plane surface 111 meets with the plane surface 112 forms a V-shaped sunken bottom 113.

When the body 110 of the attachment 100 is disposed on the V-block prism 1, the top 105 of the body 110 opposes and contacts closely with the bottom 113 of the groove 11. As a result, the recess 106 formed on the top 105 of the body 110 is blocked by the bottom 113 of the groove 11. A space defined by the sealed recess 106 forms an enclosing space 107 for enclosing the liquid sample.

That is, the enclosing space 107 for enclosing the liquid sample is formed between the surface (the bottom 113) of the groove 11 formed on the V-block prism 1 and the body 110 (the recess 106) of the attachment 100. As shown by the hatching in FIG. 4, by enclosing the liquid sample in the enclosing space 107, the enclosed liquid sample can be kept in a state of directly contacting with the surface (the bottom 113) of the groove 11.

As for the enclosing space 107, a length L along the groove 11 is about 3 mm, and a thickness T in the front-back direction is about 1 mm. In this way, the recess 106 (the enclosing space 107) has an extremely small volume, and is capable of utilizing capillarity phenomenon to take the liquid sample into the recess 106. After the liquid sample is taken into the recess 106, even if in a state of making the recess 106 facing downward as shown in FIG. 3A and FIG. 3B, the liquid sample can be prevented from falling out of the recess 106 by the surface tension of the liquid sample, and the body 110 can be disposed on the groove 11 in this state.

The material of the body 110 is for example, a light impermeable material, or a material difficult for the light to transmit through. Or the surface of the recess 106 of the body 110 may be coated with a light impermeable material, or a material difficult for the light to transmit through. However, the disclosure is not limited to such a structure and the body 110 can be formed by any material.

As shown in FIG. 4, the measuring beam is incident perpendicularly on one end surface 12 of the V-block prism 1. The measuring beam incident from the end surface 12 passes through the V-block prism 1 and is incident from the plane surface 111 of the groove 11 to the liquid sample in the enclosing space 107. At this point, as shown by the arrow in FIG. 4, the measuring beam refracts at an angle corresponding to the refractive index of the liquid sample, transmits through the liquid sample, then refracts again at a plane surface 112 of the groove 11 and is incident on the V-block prism 1. Then, the measuring beam passes through the V-block prism 1 and refracts again when being emitted from the other end surface 13.

In this way, the measuring beam is irradiated to the liquid sample via the V-block prism 1, and the measuring beam transmitted through the liquid sample is emitted from the other end surface 13 at an angle corresponding to the refractive index difference between the V-block prism 1 and the liquid sample. Therefore, by detecting the measuring beam emitted from the V-block prism 1, the refractive index of the liquid sample can be measured based on the emitting angle of the measuring beam (measuring step).

3. Effects (1) In the embodiment, the attachment 100 is disposed so as to enter the V-shaped the groove 11 formed on the V-block prism 1, thereby the enclosing space 107 can be formed between the attachment 100 and the surface of the V-shaped groove 11. The liquid sample enclosed in the enclosing space 107 is made to contact directly with the surface of the groove 11, thereby the enclosing space 107 can be formed with a relatively small volume, thus the consumption amount of the liquid sample can be effectively reduced.

(2) Besides, in the embodiment, the recess 106 is formed on the top 105 of the body 110 of the attachment 100, thereby the enclosing space 107 with a relatively small volume can be easily formed between the recess 106 and the surface of the V-shaped groove 11.

4. A First Variation Example of the Attachment

Figure 5A:
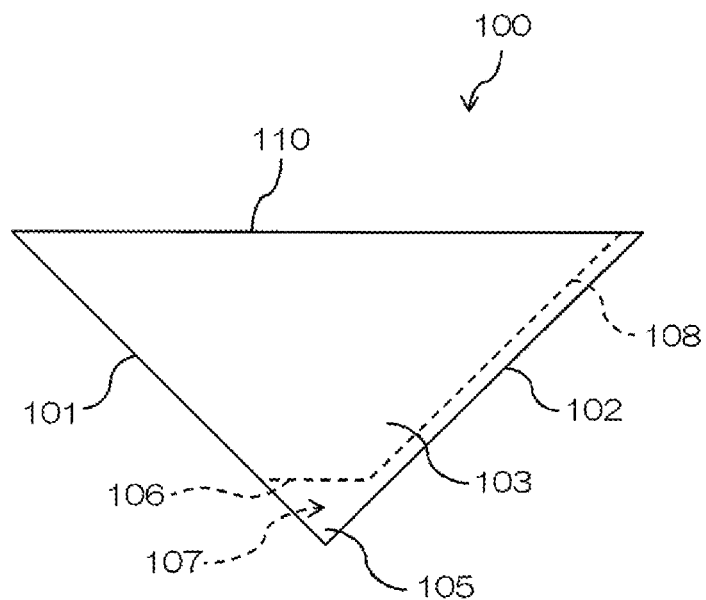
FIG. 5A is a front view illustrating a first variation example of the attachment.
Figure 5B:
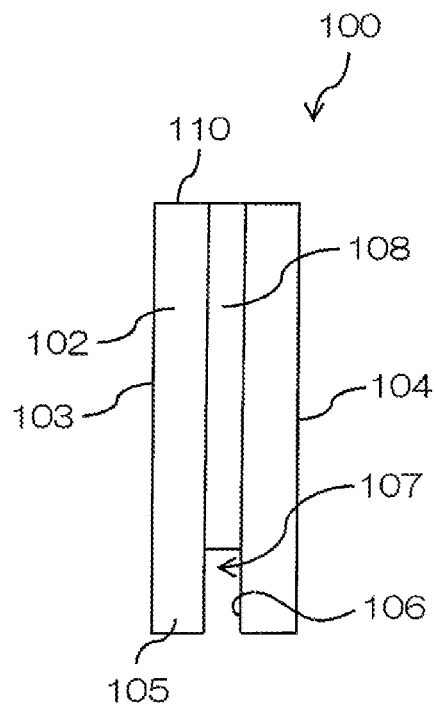
FIG. 5B is a side view of the attachment in FIG. 5A.

FIG. 5A is a front view illustrating a first variation example of the attachment 100. FIG. 5B is a side view of the attachment 100 in FIG. 5A. The first variation example is different from the above embodiment in that a groove part 108 is formed on the body 110 of the attachment 100. Other aspects are the same as those of the above embodiment, and thus the same structure is denoted by the same symbol in the drawings and detailed description is omitted.

The groove part 108 is formed on the side surface 102 of the body 110. Specifically, the groove part 108 extends from one end of the side surface 102 (the top 105) of the body 110 to the other end (the side opposite to the top 105), and communicates with the recess 106. When such a body 110 is disposed on the V-block prism 1, a state that the groove part 108 communicates with the enclosing space 107 is achieved. That is, the enclosing space 107 is open to the outside via the groove part 108.

Therefore, via the groove part 108 formed on the side surface 102 of the body 110 of the attachment 100, the liquid sample can be easily filled in the enclosing space 107 communicating with the groove part 108. However, the groove part 108 may also be formed on the side surface 101 on an opposite side instead of on the side surface 102 of the body 110. Besides, the groove part 108 may also be formed on the two side surfaces 101, 102 of the body 110.

5. A Second Variation Example of the Attachment

Figure 6A:
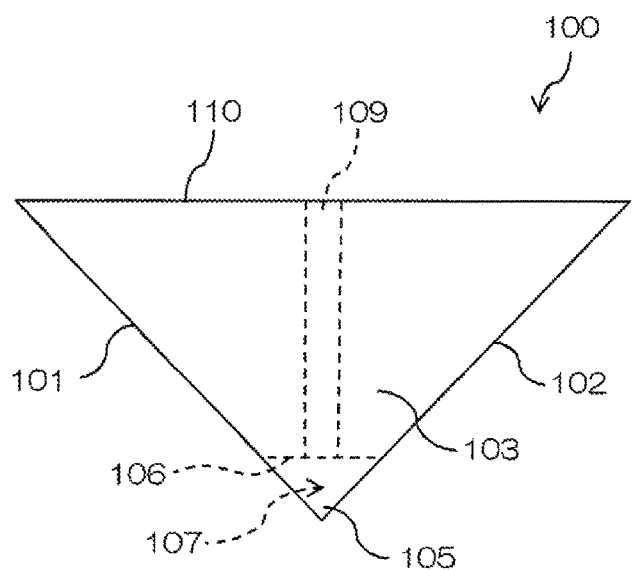
FIG. 6A is a front view illustrating a second variation example of the attachment.
Figure 6B:
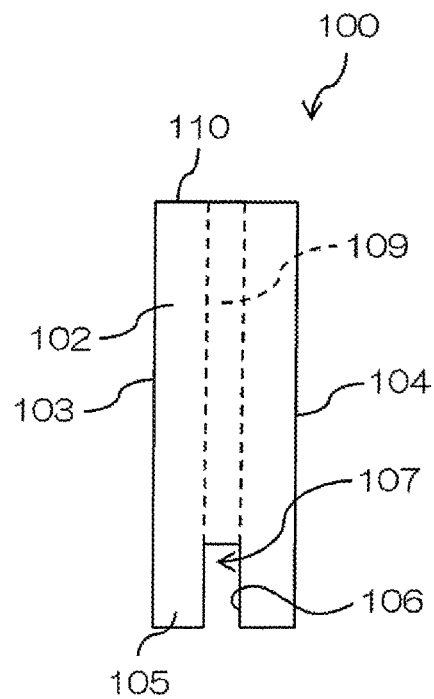
FIG. 6B is a side view of the attachment in FIG. 6A.

FIG. 6A is a front view illustrating a second variation example of the attachment 100. FIG. 6B is a side view of the attachment 100 in FIG. 6A. The second variation example is different from the above embodiment in that a through hole 109 is formed on the body 110 of the attachment 100. Other aspects are the same as those of the above embodiment, and thus the same structure is denoted by the same symbol in the drawings and detailed description is omitted.

The through hole 109 is formed so as to penetrate through the body 110 from one end (the top 105) to the other end (the side opposite to the top 105), and communicates with the recess 106. When such a body 110 is disposed on the V-block prism 1, a state that the through hole 109 communicates with the enclosing space 107 is achieved. That is, the enclosing space 107 is open to the outside via the through hole 109.

Therefore, via the through hole 109 formed inside the body 110 of the attachment 100, the liquid sample can be easily filled in the enclosing space 107 communicating with the through hole 109. However, the through hole 109 is not limited to such a structure which extends straight in the vertical direction as shown in FIG. 6A and FIG. 6B, and may be a curved or bended shape. In addition, a plurality of through holes 109 may be formed on the body 110.

6. A Third Variation Example of the Attachment

Figure 7A:
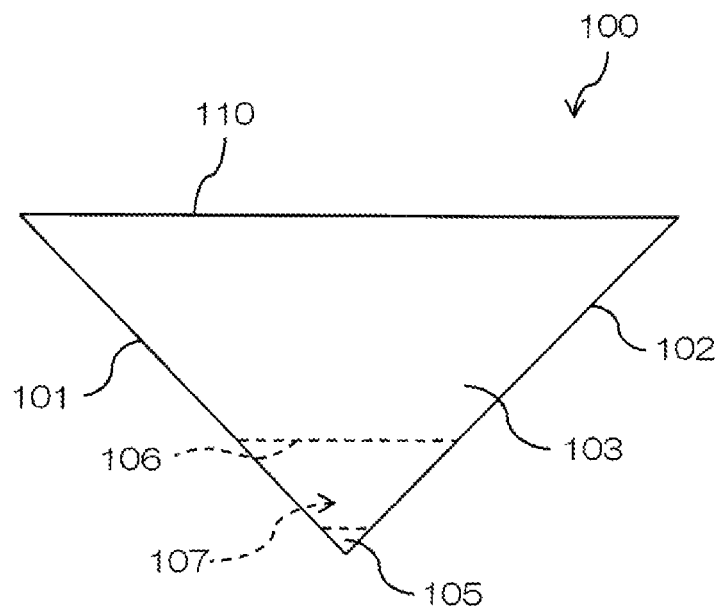
FIG. 7A is a front view illustrating a third variation example of the attachment.
Figure 7B:
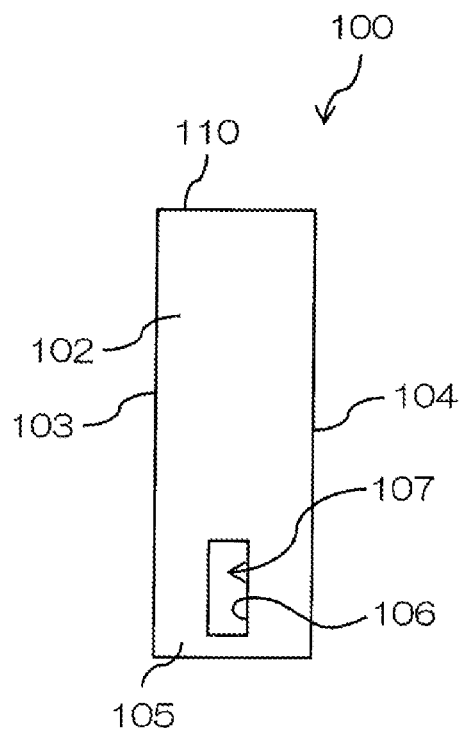
FIG. 7B is a side view of the attachment in FIG. 7A.

FIG. 7A is a front view illustrating a third variation example of the attachment 100. FIG. 7B is a side view of the attachment 100 in FIG. 7A. The third variation example is different from the above embodiment in the shape of the recess 106 formed on the body 110 of the attachment 100. Other aspects are the same as those of the above embodiment, and thus the same structure is denoted by the same symbol in the drawings and detailed description is omitted.

In the third variation example, the recess 106 is not a sunken shape heading from the top 105 of the body 110 toward the central part side as in the above embodiment, and is formed by a through hole penetrating from the side surface 101 of the top 105 to the side surface 102. When such a body 110 is disposed on the V-block prism 1, a state that the recess 106 serving as a through hole is blocked by the side surfaces 101, 102 of the groove 11 is achieved, and the space defined by the sealed recess 106 forms the enclosing space 107 for enclosing the liquid sample.

Even in such a structure, the enclosing space 107 with a relatively small volume can be easily formed between the recess 106 and the surface of the V-shaped the groove 11 as in the above embodiment. However, a groove part communicating with the recess 106 may also be formed as in the first variation example, or a through hole communicating with the recess 106 may also be formed as in the second variation example.

7. A Fourth Variation Example of the Attachment

Figure 8:
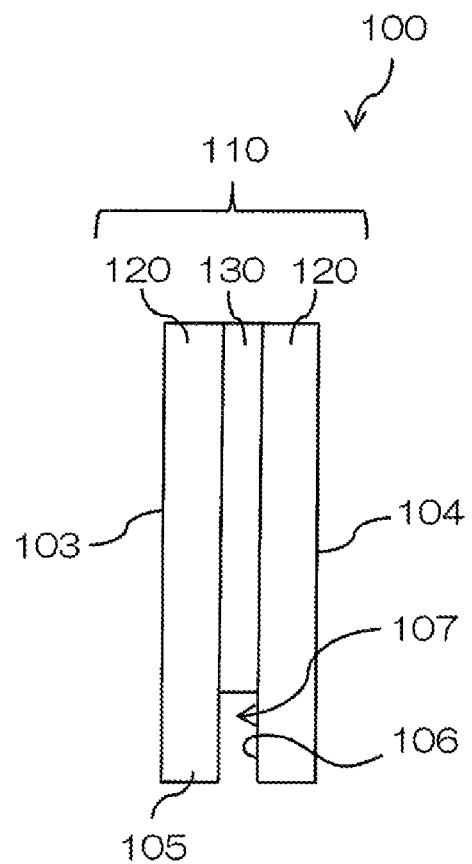
FIG. 8 is a side view illustrating a fourth variation example of the attachment.

FIG. 8 is a side view illustrating a fourth variation example of the attachment 100. The fourth variation example is different from the above embodiment in that the body 110 of the attachment 100 is formed by a plurality of members. Other aspects are the same as those of the above embodiment, and thus the same structure is denoted by the same symbol in the drawings and detailed description is omitted.

In the fourth variation example, the body 110 is provided with a pair of side plates 120 and a spacer 130. The spacer 130 is sandwiched between the pair of side plates 120. In this way, the body 110 becomes a structure in which the pair of side plates 120 and the spacer 130 are formed integrally.

An end in the spacer 130 on the top 105 side of the body 110 enters deeper on the central part side of the body 110 than the pair of side plate 120. That is, the ends of the top 105 of the pair of side plates 120 protrude more than the spacer 130. Accordingly, the recess 106 defined by the pair of side plate 120 and the spacer 130 is formed on the top 105 of the body 110.

When such a body 110 is disposed on the V-block prism 1, a state that the recess 106 is blocked by the bottom 113 of the groove 11 is achieved, and the space defined by the sealed recess 106 forms the enclosing space 107 for enclosing the liquid sample. Therefore, the body 110 of the attachment 100 can be formed by the pair of side plates 120 and the spacer 130, and the enclosing space 107 can be formed between the body 110 and the surface (the bottom 113) of the V-shaped the groove 11 formed on the V-block prism 1.

However, a groove part communicating with the recess 106 may also be formed as in the first variation example, or a through hole communicating with the recess 106 may be formed as in the second variation example. Besides, the recess 106 may also be formed by a through hole as in the third variation example by forming a through hole which penetrates from the side surface 101 to the side surface 102 on a part of the spacer 130 on the top 105 of the body 110, or by sandwiching a plurality of separated spacers 130 between the pair of side plates 120 to form the through hole.

According to such a structure, the attachment for liquid sample measurement is disposed so as to enter the V-shaped groove formed on the V-block prism, by which the enclosing space can be formed between the attachment and the surface of the V-shaped groove. By making the liquid sample enclosed in the enclosing space contact directly with the surface of the groove, the enclosing space can be formed with a relatively small volume, thus the consumption amount of the liquid sample can be effectively reduced.

When the body is disposed on the V-block prism, a recess which defines the enclosing space may be formed on a top of the body which opposes a bottom of the groove.

According to such a structure, by forming a recess on the top of the body of the attachment for liquid sample measurement, an enclosing space with a relatively small volume can be easily formed between the recess and the surface of the V-shaped groove.

When the body is disposed on the V-block prism, a groove part which communicates with the enclosing space may be foil red on a side surface of the body.

According to such a structure, the liquid sample can be easily filled in the enclosing space communicating with the groove part via the groove part which is formed on the side surface of the body of the attachment for liquid sample measurement.

When the body is disposed on the V-block prism, a through hole which communicates with the enclosing space may be formed inside the body.

According to such a structure, the liquid sample can be easily filled in the enclosing space communicating with the through hole via the through hole which is formed inside the body of the attachment for liquid sample measurement.

The body may include a pair of side plates and a spacer sandwiched between the pair of side plates. In this case, the enclosing space may be formed between a space, defined by the pair of side plates and the spacer, and the surface of the groove formed on the V-block prism.

According to such a structure, the pair of side plates and the spacer are used to form the body of the attachment for liquid sample measurement, and an enclosing space can be formed between the body and the surface of the V-shaped groove formed on the V-block prism.

Effect

According to the disclosure, an enclosing space is formed between the attachment for liquid sample measurement and the surface of the V-shaped groove formed on the V-block prism, and the liquid sample enclosed in the enclosing space is made to directly contact with the surface of the groove, thereby the enclosing space can be formed with a relatively small volume, thus the consumption amount of the liquid sample can be effectively reduced.

What is claimed is:

1. An attachment for liquid sample measurement, which is disposed on a V-block prism with a groove which is a V-shaped groove for keeping a liquid sample formed thereon so as to enter the groove, and is used when a refractive index of the liquid sample is measured by a V-block refractive index measuring device, the attachment for liquid sample measurement comprising:

a body, which forms an enclosing space for enclosing the liquid sample between the body and a surface of the groove formed on the V-block prism, and makes the liquid sample enclosed in the enclosing space contact directly with the surface of the groove.

2. The attachment for liquid sample measurement according to claim 1, wherein when the body is disposed on the V-block prism, a recess which defines the enclosing space is formed on a top of the body which opposes a bottom of the groove.

3. The attachment for liquid sample measurement according to claim 1, wherein when the body is disposed on the V-block prism, a groove part which communicates with the enclosing space is formed on a side surface of the body.

4. The attachment for liquid sample measurement according to claim 1, wherein when the body is disposed on the V-block prism, a through hole which communicates with the enclosing space is formed inside the body.

5. The attachment for liquid sample measurement according to claim 1, wherein the body comprises a pair of side plates and a spacer sandwiched between the pair of side plates, and the enclosing space is formed between a space, defined by the pair of side plates and the spacer, and the surface of the groove formed on the V-block prism.

6. A refractive index measuring device, comprising:

the attachment for liquid sample measurement according to claim 1;

the V-block prism, on which the attachment for liquid sample measurement is disposed;

a light source part, which irradiates a measuring beam to the liquid sample enclosed in the enclosing space via the V-block prism; and a detector, which detects the measuring beam transmitted through the liquid sample.

7. A refractive index measuring method, comprising:

an attachment disposing step, in which an attachment for liquid sample measurement is disposed on a V-block prism on which a groove which is a V-shaped groove for keeping a liquid sample so as to enter the groove, thereby forming an enclosing space for enclosing the liquid sample between a surface of the groove formed on the V-block prism and the attachment for liquid sample measurement; and a measuring step, in which a measuring beam is irradiated, via the V-block prism, to the liquid sample enclosed in the enclosing space so as to contact directly with the surface of the groove, thereby detecting the measuring beam transmitted through the liquid sample and measuring a refractive index of the liquid sample.

* * * * *